(12) United States Patent
Landwehr

(10) Patent No.: US 11,633,161 B2
(45) Date of Patent: Apr. 25, 2023

(54) DEVICE AND PROCESS FOR PROVIDING A SUGGESTION FOR AN ADAPTED ALARM CONDITION FOR A MEDICAL SYSTEM USER

(71) Applicant: Drägerwerk AG & Co. KGaA, Lübeck (DE)

(72) Inventor: Birger Landwehr, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 0 days.

(21) Appl. No.: 17/511,828

(22) Filed: Oct. 27, 2021

(65) Prior Publication Data

US 2022/0133244 A1    May 5, 2022

(30) Foreign Application Priority Data

Nov. 3, 2020   (DE) .................... 10 2020 128 948.0

(51) Int. Cl.
| | | |
|---|---|---|
| *A61B 5/00* | (2006.01) | |
| *G08B 21/02* | (2006.01) | |
| *G08B 29/18* | (2006.01) | |

(52) U.S. Cl.
CPC ............ *A61B 5/746* (2013.01); *A61B 5/0002* (2013.01); *G08B 21/02* (2013.01); *G08B 29/185* (2013.01)

(58) Field of Classification Search
CPC ...... A61B 5/746; A61B 5/0002; G08B 21/02; G08B 29/185; G08B 23/00
See application file for complete search history.

(56) References Cited

U.S. PATENT DOCUMENTS

| | | | |
|---|---|---|---|
| 9,700,218 B2 * | 7/2017 | Boyer | .................... A61B 5/746 |
| 10,123,729 B2 * | 11/2018 | Dyell | ..................... A61B 5/162 |
| 2016/0022140 A1 | 1/2016 | Colman et al. | |
| 2017/0000424 A1 * | 1/2017 | Friedman | ........... A61B 5/14542 |
| 2019/0295696 A1 | 9/2019 | Yang et al. | |
| 2019/0325332 A1 * | 10/2019 | Swisher | ................. G16H 50/30 |

FOREIGN PATENT DOCUMENTS

| | | |
|---|---|---|
| DE | 102013111084 A1 | 4/2015 |
| DE | 112016002992 T5 | 3/2018 |
| EP | 1449558 B1 | 7/2013 |

* cited by examiner

*Primary Examiner* — John A Tweel, Jr.
(74) *Attorney, Agent, or Firm* — McGlew and Tuttle, P.C.

(57) ABSTRACT

A device, process and computer program based process provide a suggestion for at least one adapted alarm condition for a user in a medical system. The device includes a processing device configured to generate at least one adapted alarm condition of an alarm concerning at least one parameter triggering the alarm. The alarm condition is provided to offer to the user a possibility of adapting the alarm condition when an alarm frequency exceeds a limit value. The device further includes an interface, which is configured to provide the suggestion for the at least one adapted alarm condition of the alarm. The process includes the generation of at least one adapted alarm condition of an alarm concerning at least one parameter triggering the alarm. This adapted alarm condition is provided to offer the user the possibility of adapting the alarm condition when an alarm frequency exceeds a limit value.

19 Claims, 2 Drawing Sheets

DEVICE AND PROCESS FOR PROVIDING A SUGGESTION FOR AN ADAPTED ALARM CONDITION FOR A MEDICAL SYSTEM USER

CROSS REFERENCE TO RELATED APPLICATIONS

This application claims the benefit of priority under 35 U.S.C. § 119 of German Application 10 2020 128 948.0, filed Nov. 3, 2020, the entire contents of which are incorporated herein by reference.

TECHNICAL FIELD

The present invention pertains to a device, to a process as well as to a computer program process for providing a suggestion for at least one adapted alarm condition for a user in a medical system, especially but not exclusively to a concept for adapting alarm conditions in a medical system after repeated, clinically irrelevant alarms, which have remained without a countermeasure having been taken in the medical system.

TECHNICAL BACKGROUND

Medical systems, for example, ventilators, have an alarm function in order to draw the attention of nursing staff to a critical situation of the patient or to a technical event. A technical event may be, for example, a technical disturbance of the medical system. The monitoring of ventilation parameters as well as of technical device components is a key task of modern ventilators. If a deviation of the measured values being monitored or even a technical disturbance of the device develops during the therapy, an alarm is outputted for the clinical staff via the installed speaker. Standard settings are frequently used in a clinical setting for therapy and alarm conditions, which pertain to at least one parameter triggering the alarm. It may happen in clinical practice that the alarm limits are not always set optimally for the state of the patient. This may lead to an increase in the frequency of clinically irrelevant alarms based on excessively conservative alarm conditions and hence to a high workload for the nursing staff. In addition, an increase in the frequency of alarms due to frequent acoustic disturbances may cause additional stress for the nursing staff and for the patients.

The causes of a lack of setting or adaptation of alarm conditions may be complex. There may not be any clear control of the areas of responsibility for the nursing staff, or the nursing staff may not be authorized to carry out settings on the medical system. Furthermore, there may be uncertainties in the setting of the limit values due to concerns that a clinically relevant alarm situation might not be detected soon enough.

The workload may often be high in the wards, and the nursing activities may be interrupted by recurring alarms in such situations. Even in the case that the patient's situation can be detected, the acoustic alarm signal can only be muted for a certain time, usually for 2 minutes. It may happen that a countermeasure to be taken by the nursing staff to eliminate the cause of the alarm cannot take place immediately for various reasons after the alarm has been muted.

The patent document EP 1449558 B1 pertains to a system and to a process for setting and displaying ventilation alarms. An analysis text, the root cause and dependent subsequent alarms are outputted here for each indicated alarm.

The patent document US 2019/295696 A1 pertains to a process in which individualized alarm limits are determined on the basis of patient data and are suggested to the user.

SUMMARY

Therefore, there is a need against this background to provide an improved alarm function in a medical system, which alarm function can reduce the workload of a nursing staff and/or frequent acoustic disturbances. This need is met by the device and process embodiments according to the invention.

Exemplary embodiments are based on the core idea of making it possible for the user to adapt the at least one alarm condition, for example, to the current situation. At least one adapted alarm condition of an alarm concerning at least one parameter triggering the alarm is generated for this purpose, and this alarm condition is provided to the user for release or confirmation. The alarm condition can be adapted hereby, for example, to the state of the patient during the course of the therapy. An adequate setting of alarm conditions is generally of considerable significance. If, for example, the alarm conditions are too far from the measured parameters, a life-threatening situation may not possibly be able to be detected by the device. If, contrary to this, the alarm conditions are set too narrowly, a high number of clinically irrelevant alarms can usually be expected. Furthermore, the trend of individual parameters may shift in the course of the therapy, so that an adaptation of the alarm conditions may become necessary for this reason as well.

Exemplary embodiments lead to a device for providing a suggestion for at least one adapted alarm condition for a user in a medical system. The device comprises a processing device, which is configured to generate at least one adapted alarm condition of an alarm concerning at least one parameter triggering the alarm. The adapted alarm condition is provided to the user for release or confirmation in order to offer to the user a possibility of adapting the at least one alarm condition when an alarm frequency exceeds a limit value. The device comprises, furthermore, an interface, which is configured to provide the suggestion for the at least one adapted alarm condition of the alarm. Exemplary embodiments can thus make possible an adaptation of one or more alarm conditions, for example, to the state of the patient during the course of the therapy with a favorable effort. The workload of the nursing staff and/or frequent acoustic signals can be reduced thereby.

The processing device may further be configured to indicate at least one possible cause for the alarm and at least one possibility of eliminating the at least one possible cause of the alarm when the alarm frequency exceeds the limit value. The interface may be configured to provide the at least one possible cause of the alarm and the at least one possibility for eliminating the at least one possible cause of the alarm. The nursing staff can be assisted by a corresponding configuration to eliminate the alarm as well as its cause rapidly and reliably or to configure it corresponding to the conditions.

Furthermore, the processing device may be configured to generate the at least one adapted alarm condition when no user action to eliminate the at least one possible cause of the alarm takes place within a predefined time period. This can prevent a large number of suggestions from being made for the adapted alarm conditions. In particular, such suggestions may not take place when the alarm entails a user action. A definition or adaptation of a definition of the alarm conditions can thus be made possible as a function of the user action that does not take place.

For example, the processing device may be configured, furthermore, to determine on the basis of video data whether at least one user action to eliminate the at least one possible cause of the alarm has taken place. An automatic detection of the user action having taken place can be made possible in this case.

The processing device may furthermore be configured in some exemplary embodiments to store information on whether at least one user action to eliminate the at least one possible cause of the alarm has taken place. Exemplary embodiments can thus make it possible to poll the user action that has taken place at a later time, for example, for the purpose of generating an adapted alarm condition.

In other exemplary embodiments, the processing device may further be configured to generate the at least one adapted alarm condition when a frequency of actions to suppress the alarm exceeds a predefined threshold value. The suppression of the alarm may comprise a suppression of an acoustic alarm generation by means of silence/audio off. A visual display of the alarm may be preserved in this case. The suppression of the alarm or the suppression of an acoustic alarm generation may be an indication that the alarm conditions have been selected incorrectly for the current situation and the increase in the alarm frequency, which has been brought about thereby, is suppressed by the nursing staff. The adaptation of the alarm conditions can be further simplified for the nursing staff members in this case.

The processing device may further be configured in exemplary embodiments to store at least one alarm, the time thereof, at least one alarm condition of the alarm, vital data of a patient and/or the actions taken to suppress the alarm. The generation of at least one adapted alarm condition, which is, for example, adapted individually to the particular state of the patient during the therapy, can thus be improved further.

These stored data may further be used for the processing device. The processing device may further be configured to determine a trend of a vital parameter on the basis of the vital data of the patient. The trend of the vital parameter can make it possible to monitor how the state of the patient is changing during the therapy.

The processing device may further be configured in some exemplary embodiments to classify alarms in a classification by means of the at least one parameter triggering the alarm. The classification of the alarms on the basis of the at least one parameter generating the alarm can further improve the generation of the at least one adapted alarm condition adapted to the current situation.

The processing device can furthermore be configured in this connection to store the classification of the alarm. This can make possible a monitoring and recording of the time course of the alarm as well as the classification thereof in order to correspondingly adapt the generation of the at least one adapted alarm condition on the basis of these data.

Furthermore, the processing device may be configured to check whether a plurality of actions have taken place to suppress the alarm in case of an identical classification of the alarm. This can adapt the generation of the at least one adapted alarm condition to the particular situation even better and thus improve it further and it can also adapt the generation of adapted alarm conditions to alarms of different classifications.

The processing device may further be configured in some exemplary embodiments to store at least one technical event of the device or of an apparatus connected to the device as well as the alarm condition. A technical event may be, for example, a technical disturbance of the device or of an apparatus connected to the device. This can improve the estimation of the current situation as well as further simplify the indication of a possible cause of the alarm as well as of at least one possibility of eliminating the at least one possible cause of the alarm.

The processing device may further be configured in other exemplary embodiments to detect a request for help of the user and to forward this to at least one other person. As a result, the nursing staff can use the help of the additional person rapidly and in a simple manner.

The interface may be configured to receive an alarm signal, and the processing device may be configured to determine information concerning the alarm frequency on the basis of the alarm signal. This can make possible a simple and reliable determination of the alarm frequency.

Exemplary embodiments lead, furthermore, to a process for providing a suggestion for adapted alarm conditions for a user in a medical system. The process comprises the generation of at least one adapted alarm condition of an alarm concerning at least one parameter triggering the alarm. The adapted alarm condition is provided to the user for release or confirmation in order to offer to the user a possibility of adapting the at least one alarm condition when an alarm frequency exceeds a limit value. A high workload of the nursing staff and/or frequent acoustic signals can be reduced by the adaptation of the alarm conditions based on an automatically generated suggestion, for example, on the basis of the current situation.

Another exemplary embodiment is a computer program with a program code for carrying out a process being described here when the program code is executed on a computer, on a processor or on a programmable hardware component. A machine-readable data storage medium is another exemplary embodiment.

Some examples of devices and/or processes will be explained in more detail below with reference to the attached figures only as examples. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
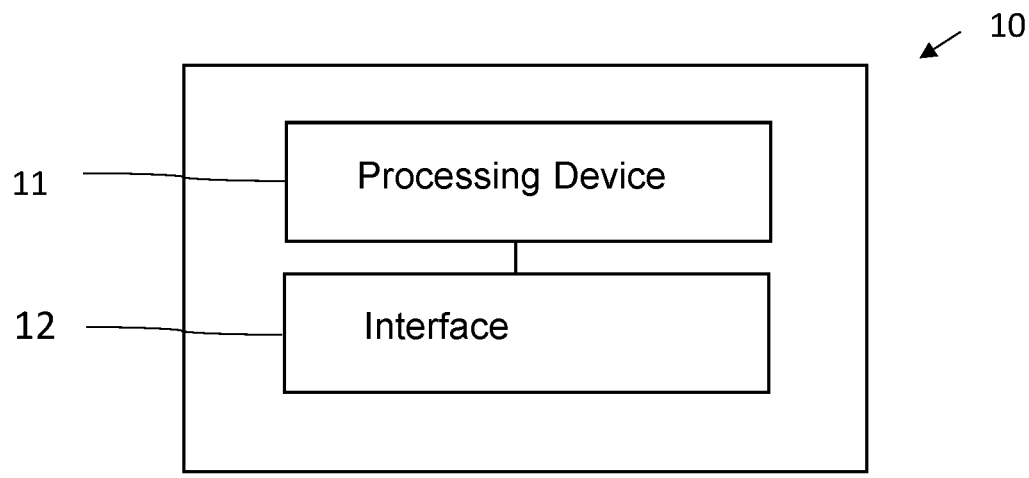
FIG. 1 is a block diagram of an exemplary embodiment of a device for providing a suggestion for at least one adapted alarm condition for a user in a medical system.

Referring to the drawings, different examples will be described below in more detail with reference to the attached figures. The thicknesses of lines, layers and/or areas may be exaggerated for illustration in the figures.

Further examples may cover modifications, equivalences and alternatives, which fall within the scope of the disclosure. Identical or similar reference numbers pertain in the entire description of the figures to identical or similar elements, which may be implemented identically or in a modified form in a comparison with one another, while they provide the same function or a similar function.

It is apparent that when an element is described as being "connected" to or "coupled" with another element, the elements may be connected or coupled directly or via one or more intermediate elements. When two elements A and B are combined with the use of an "or," this should be understood to be such that all possible combinations are disclosed, i.e., only A, only B as well as A and B unless something else is explicitly or implicitly defined. An alternative wording for the same combinations is "at least one of A and B" or "A and/or B." The same applies, mutatis mutandis, to combinations of more than two elements.

FIG. 1 shows a block diagram of an exemplary embodiment of a device 10 for providing a suggestion for at least one adapted alarm condition for a user in a medical system. The medical system may be configured, for example, in the form of a ventilator or of a heart rate-measuring device. The device 10 comprises a processing device 11 configured to generate at least one adapted alarm condition of an alarm concerning at least one parameter generating an alarm, which alarm condition is provided to the user in order to offer to the user a possibility of adapting the at least one alarm condition when an alarm frequency exceeds a limit value. The processing device 11 may be configured in the form of a processor, especially in the form of a system-on-a-chip.

The processing device 11 may comprise in exemplary embodiments any one or more freely selectable controllers, microcontrollers, network processors, processor cores, such as digital signal processor cores (DSPs), programmable hardware components, etc. Exemplary embodiments are not limited here to a particular type of processor core. Any one of processor cores or even a plurality of processor cores or microcontrollers are conceivable for the implementation of a processing device 11. Implementations in an integrated form with other devices, for example, in a control unit that additionally also comprises one or more other functions, are also conceivable. A processing device 11 may be embodied in exemplary embodiments by a processor core, by a computer processor core (CPU=Central Processing Unit), by a graphics processor core (GPU=Graphics Processing Unit), by an application-specific integrated circuit core (ASIC=Application-Specific Integrated Circuit), by an integrated circuit (IC=Integrated Circuit), by a one-chip system core (SOC=System on Chip), by a programmable logic element or a field-programmable gate array with a microprocessor (FPGA=Field Programmable Gate Array) as the core of the component or components.

Examples of the parameter triggering the alarm may be a respiration rate, a blood pressure and/or a heart rate of the patient. The alarm condition may pertain in this case to an exceeding or undershooting of a respiration rate, of a blood pressure and/or of the heart rate, which may be clinically relevant. A limit value for the alarm frequency may be defined as an absolute value, for example, at least 3, at least 5 or at least 10 alarms. As an alternative, the limit value for the alarm frequency may be defined relatively as a function of the time, for example, at least two alarms in the last 5 minutes or at least two alarms in the last 10 minutes. The device 10 further comprises an interface 12, which is configured to provide the suggestion for the at least one adapted alarm condition of the alarm (an output) and which is coupled or connected to the processing device 11. The interface 12 may be configured, for example, in the form of a machine interface or in the form of a software interface.

The interface 12 may be configured in exemplary embodiments as a typical interface for communication in networks or between network components or medical devices. For example, the interface may be configured in exemplary embodiments by corresponding contacts. It may also be configured in exemplary embodiments as separate hardware and comprise a memory, which stores the signals to be transmitted or received at least temporarily. The interface 12 may be configured to receive electrical signals, for example, as a bus interface, as an optical interface, as an Ethernet interface, as a wireless interface, as a field bus interface, etc. It may, moreover, be configured in exemplary embodiments for wireless transmission and comprise a radio front end as well as corresponding antennas.

The processing device 11 may further be configured to indicate at least one possible cause of an alarm and at least one possibility for eliminating the at least one possible cause of the alarm when the alarm frequency exceeds the limit value. The elimination of the cause may also comprise, in principle, the setting of an alarm condition such that clinically irrelevant individual events do not necessarily lead to an alarm generation. An analysis of the causes of the alarm may be carried out, for example, as described below. An analysis of the root cause of the alarm may be carried out. An example of a cause of the alarm may be a technical disturbance of the medical system or even vital data of the patient, which are in a clinically critical range. Examples of a technical disturbance may be an interrupted connection between components of the medical system or an absence of an external power supply for the medical system. Vital data of the patient may be, for example, the respiration rate, blood pressure or heart rate. A possibility of eliminating the cause of the alarm may be the elimination of a technical disturbance of the medical system, for example, restoration of the interrupted connection between components of the medical system or restoration of the external power supply of the medical system. As an alternative, the cause of the alarm may be eliminated. for example, by a dose adjustment of the medication being administered, by an interruption of the administration of the medication, by the administration of a different medication or by another medical treatment, for example, cardiac massage or the application of a defibrillator.

The interface 12 may further be configured to provide the at least one possible cause of the alarm and the at least one possibility of eliminating the at least one possible cause of the alarm. The interface 12 may be connected, for example, to a patient monitor, which outputs to the nursing staff the at least one possible cause of the alarm and the at least one possibility of eliminating the at least one possible cause of the alarm. The at least one possible cause of the alarm may be displayed to the nursing staff optionally with a list of additional alarms, which are caused by this, for example, a disconnection alarm.

The processing device 11 may further be configured to generate the at least one adapted alarm condition when no user action is carried out to eliminate the at least one possible cause of the alarm within a predefined time period. The processing device 11 may further be configured to determine on the basis of video data whether at least one user action takes place to eliminate the at least one possible cause of the alarm. The processing device 11 may further be configured to store information on whether at least one user action takes place to eliminate the at least one possible cause of the alarm. Possible user actions to eliminate the at least one possible cause of the alarm may be, for example, a start, interruption or dose adjustment of the administration of a medication to the patient, medical treatment of the patient, such as cardiac massage or the use of a defibrillator or restoration of the external power supply of the medical system.

The processing device 11 may further be configured to generate the at least one adapted alarm condition when the frequency of actions taken to suppress the alarm or to suppress an acoustic alarm generation exceeds a predefined threshold value. The suppression of the alarm may comprise a suppression of an acoustic alarm generation by means of silence/audio off. A visual display of the alarm may be preserved in this case. A possible threshold value for the frequency of actions taken to suppress the alarm may be, for example, the suppression of at least two consecutive alarms, of at least two alarms within 5 minutes, of at least two alarms within 10 minutes or of at least three alarms within 10 minutes.

The processing device 11 may further be configured to store at least one alarm, the time thereof, at least one alarm condition of the alarm, vital data of a patient and/or the actions taken to suppress the alarm. The past alarms can be analyzed accurately and reconstructed in this case and information obtained therefrom may optionally be used for future treatments.

The processing device 11 may further be configured to determine a trend of a vital parameter on the basis of the vital data of the patient. It is also possible, for example, to carry out an if-then analysis described below. For example, the alarm condition belonging to the alarm or the alarm limit is highlighted in color in an opened dialog, and/or a trend of the vital parameter over a time period is displayed. Different embodiments and their combinations may be provided in this connection. The opened dialog may be displayed, for example, on the patient monitor, which is connected to the device 10. The time period may relate, for example, to a time period during which the nursing staff has not eliminated the cause but has only activated an audio off/silence function. The silence function (frequently also called audio pause) mutes the acoustic alarm for a limited time (for example, 2 minutes). The audio off function mutes the acoustic alarm for an unlimited time. However, the function is, in general, deactivated automatically with the disappearance of the alarm, so that an acoustic alarm is also generated again on a repeated occurrence.

The silence function (or audio pause) can only mute the acoustic alarm signal for a certain time, as a rule, for 2 minutes. The trend of the vital parameter of the patient may be displayed, for example, over a time period of at least 5 minutes, at least 10 minutes, at least 15 minutes, at least 20 minutes or at least 30 minutes. For example, the number of alarms, which would have been outputted at the particular setting of the alarm limit, can be displayed visually with the preselection of an alarm limit. This can be used as an indicator of a predicted alarm frequency for a future time period.

The processing device 11 may be configured, furthermore, to classify alarms by means of the at least one parameter triggering the alarm in a classification. Parameters triggering the alarm may be, for example, the respiration rate, the blood pressure and/or the heart rate. The processing device 11 may further be configured to store the classification of the alarm. The processing device 11 may further be configured to check whether a plurality of actions to suppress the alarm or to suppress the acoustic alarm generation have taken place in case of the same classification of the alarm.

The processing device 11 may further be configured to store at least one technical event of the device 10 or of an apparatus connected to the device 10 as well as the alarm condition. This can make it possible to have the ability to reconstruct even later possible causes of an alarm, which may be attributable to a technical event of the device 10, which occurred in the past. A technical event may be, for example, a technical disturbance of the medical system. A technical disturbance may be, for example, an interruption of the external power supply of the medical system or an interruption of a connection between components of the medical system.

The processing device 11 may further be configured to detect a request for help of the user and to forward this to at least one other person. For example, the request for help or a call for help may be offered in a dialog with a call function, via which the nursing staff can request more help. For example, additional nursing staff can be called via this call function, or an audio and/or video connection to additional nursing staff can be established. The dialog may be displayed, for example, on the patient monitor connected to the device 10.

The interface 12 may further be configured to receive an alarm signal, and the processing device 11 may further be configured to determine information concerning the alarm frequency on the basis of the alarm signal. The alarm frequency may be outputted to the nursing staff via an opened dialog, which may be displayed, for example, on the patient monitor. The alarm frequency may be stated optionally in absolute numbers or relative to a predefined time period, for example, the last 5 minutes, the last 10 minutes, the last 15 minutes, the last 20 minutes or the last 30 minutes.

Further details and aspects are mentioned in connection with the exemplary embodiments described above or below. The exemplary embodiment shown in FIG. 1 may comprise one or more additional optional features.

Figure 2:
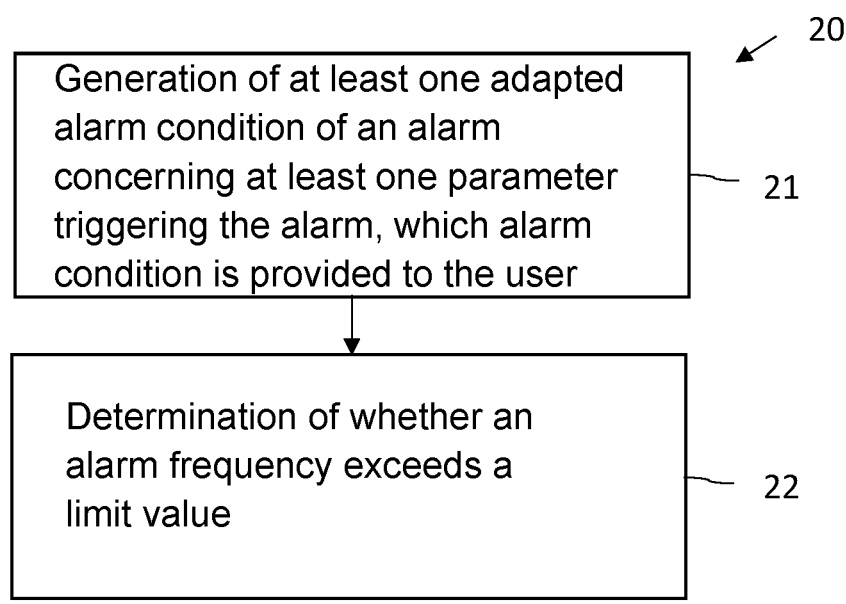
FIG. 2 is a block diagram of an exemplary embodiment of a process for providing a suggestion for adapted alarm conditions for a user in a medical system.

FIG. 2 shows a block diagram of an exemplary embodiment of a process 20 for providing a suggestion for adapted alarm conditions for a user in a medical system. The process comprises the generation 21 of at least one adapted alarm condition of an alarm pertaining to at least one parameter triggering the alarm, which is provided to the user, in order to offer the user a possibility of adapting the at least one alarm condition when an alarm frequency exceeds a limit value. The process comprises, furthermore, a determination 22 of whether an alarm frequency exceeds a limit value.

The process 20 may comprise the detection and/or an analysis of the alarm or of an alarm situation. Further, the process 20 may comprise the detection of whether the nursing staff or a user has carried out one or more user actions to eliminate the at least one possible cause of the alarm or actions to eliminate the alarm situation. Furthermore, the process 20 may open a setting aid to eliminate the alarm in a negative case, in which no user action has been carried out to eliminate the at least one possible cause of the alarm. The setting aid can offer the user selection possibilities to adapt the at least one alarm condition.

Furthermore, the process 20 may comprise the detection of a situation, in which the nursing staff has repeatedly muted an alarm without having carried out a user action to lastingly eliminate it. A help dialog, in which the alarm condition may be detectable and/or measures for eliminating the alarm may be suggested, may be displayed in this situation. The help dialog may be displayed, for example, on a patient monitor.

The process 20 may take place, for example, as follows. An apparatus connected to the device 10 for providing a suggestion for at least one adapted alarm condition for a user in a medical system may repeatedly generate a "minute volume low" alarm, from which irregular breathing of the patient can be inferred in this example. A lower alarm limit may be located close to a measured value. This measured value may always be undershot slightly and/or for a short time only, which may lead to a periodic alarm generation. Every individual "minute volume low" alarm can be perceived by the nursing staff or user and be muted, without performing a further user action on the device. This can be detected by the device 10, so that a help dialog can then be opened on a monitor, for example, on the patient monitor, for example, with the muting of the third alarm. This help dialog shows now, for example, that a lowering of a lower alarm limit by 0.2 L can lead to alarm-free breathing.

The process 20 may also take, for example, the following cyclic course. Storage of monitored measured values and formation of a trend of the measured values can take place, for example, in a first step of the process 20. The measured values may be physiological measured values, non-physiological measured values and/or a device status of the device 10 or of an apparatus of the medical system, which latter apparatus is connected to the device 10.

Physiological measured values may be, for example, vital data of the patient, such as a heart rate, a blood pressure or a respiration rate of the patient. Non-physiological measured values may be, for example, a ventilation pressure or a respiratory minute volume of a ventilator connected to the device 10. The apparatus status may comprise a time stamp and a value. An unambiguous time can be assigned to the value by means of the time stamp. The value may relate to the apparatus status. Further, the process 20 may comprise, for example, in a second step, a storage of alarm conditions under which a measured value was outside of an alarm limit. Furthermore, the process 20 may comprise, for example, in a third step, the storage of alarm conditions, during which a technical event, for example, switching from an external power supply to the internal battery or sensor calibration, was detected.

Moreover, the process 20 may have a storage of a user action or a user actions in a fourth step. Further, the process may comprise, for example, in a fifth step, a checking of whether an actuation of a temporary acoustic alarm suppression, also called audio off/silence function, took place independently from another user action or other user actions. Furthermore, the process 20 may comprise, for example, in a sixth step, a storage of data concerning alarm events during which the audio off/silence function was actuated. The process 20 may further comprise, for example, in a seventh step, a checking of whether a sequence of identical alarm events with the audio off/silence function has occurred. Moreover, the process 20 may comprise in an eighth step a checking of whether the sequence of identical alarm events with the audio off/silence function had a higher frequency compared to a predefined frequency.

Further, the process 20 may comprise, for example, in a ninth step, an opening of an alarm setting dialog for adapting at least one alarm condition. The alarm setting dialog may be displayed on the patient monitor. Furthermore, the process 20 may comprise, for example, in a tenth step, a display of a dialog with measured value trends and alarm limits. The dialog may be displayed on the patient monitor. The process 20 may comprise, for example, in an eleventh step, a display of a help for reducing alarms, e.g., in the form of an if-then analysis, and/or of a determination of a suggestion for new alarm limits.

Exemplary embodiments may be or pertain, furthermore, to a computer program with a program code for executing one or more of the above processes if the computer program, is executed on a computer, processor or a programmable hardware component or on the processing device 11. Steps, operations or processes of different above-described processes may be executed by programmed computers or processors. Examples may also cover program memory devices, e.g., digital memory media, which are machine-, processor- or computer-readable and machine-executable, processor-executable or computer-executable programs of instructions. The instructions execute some or all of the steps of the above-described processes or cause them to be executed. The program memory devices may comprise or be, e.g., digital memories (flash memories or solid state drive memories), magnetic storage media, of example, magnetic disks and magnetic tapes, hard drives or optically readable digital storage media. Further examples may also cover computers, processors or control units, which are programmed for executing the steps of the above-described processors, or (field)-programmable logic arrays ((F)PLA= (Field) Programmable Logic Arrays) or (field)-programmable gate arrays ((F)PGA−(Field) programmable gate arrays), which are programmed to execute the steps of the above-described processes.

Further details and aspects are mentioned in connection with the exemplary embodiments described above or below. The exemplary embodiment shown in FIG. 2 may comprise one or more additional optional features.

Figure 3:
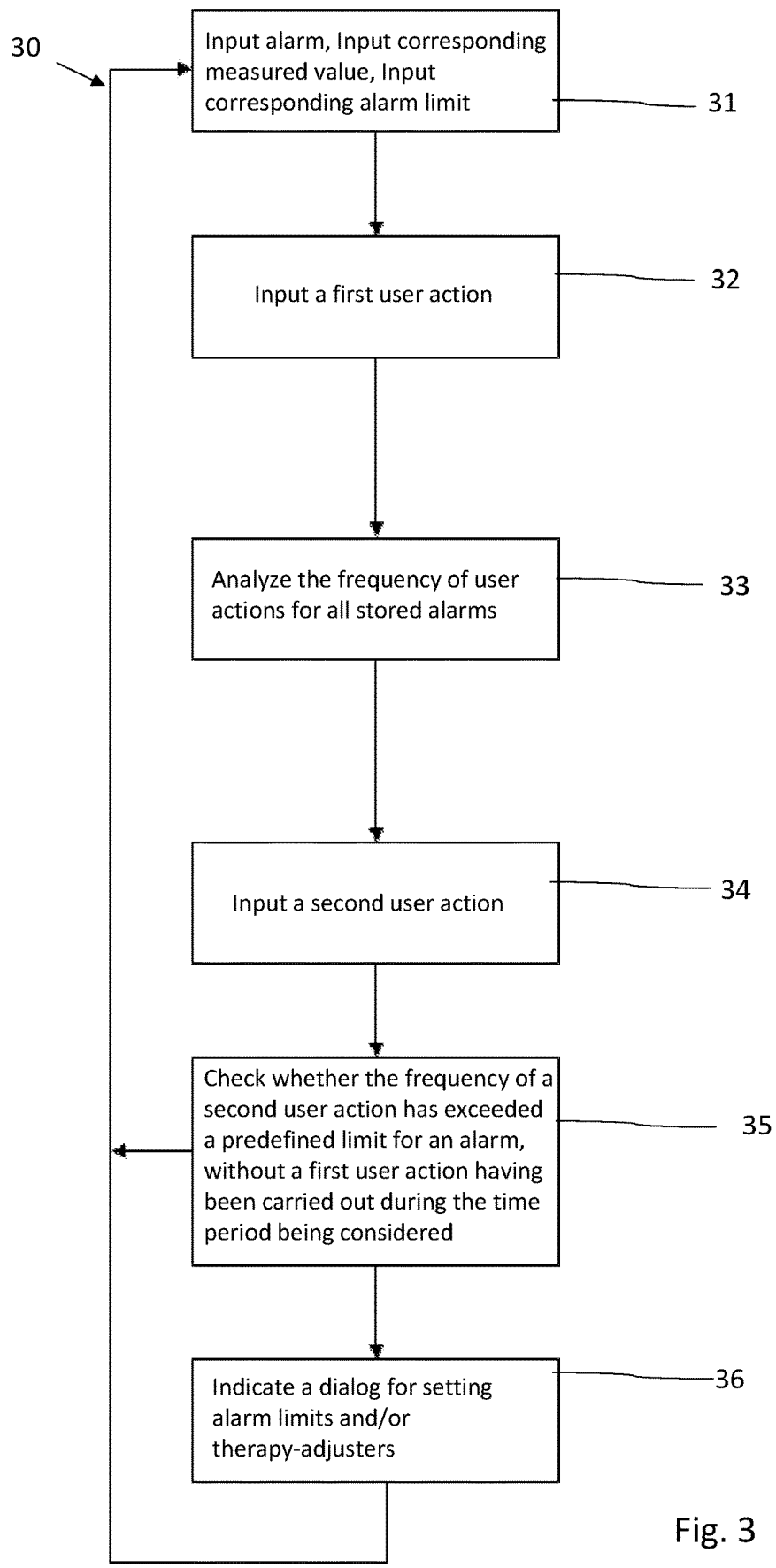
FIG. 3 is a block diagram of another exemplary embodiment of a process for providing a suggestion for adapted alarm conditions for a user in a medical system.

FIG. 3 shows a block diagram of another exemplary embodiment of a process 30 for providing a suggestion for adapted alarm conditions for a user in a medical system.

The process 30 may comprise, for example, in a first step, an input 31 of an alarm, of at least one corresponding measured value, and/or of at least one corresponding alarm condition or alarm limit or alarm limits. Each alarm and the corresponding measured values and alarm limits may be entered in this case into the memory. Alarms may also be of a technical nature, for example, leakage of a hose or leaky state of a hose of an apparatus connected to the device 10.

Further, the process 30 may comprise, for example, in a second step, an input 32 of a first user action or of first user actions. The first user action(s) may be one or more changes of therapy-relevant adjusters and/or alarm limits as well as actions performed at the patient. The latter may be transmitted, for example, by video monitoring to the device 10. The video monitoring may be approved, for example, by an accreditation commission of colleges of medicine, ACCM.

Furthermore, the process 30 may comprise, for example, in a third step, an analysis 33 of a frequency of user actions for all stored alarms. The frequency of a cause of the alarm or of an alarm cause for a time period being considered may be defined as the frequency here. Since a plurality of alarms may be selected for an alarm cause, for example, the alarms "disconnection," "airway pressure too low" or "minute volume too low" in case of disconnection of a hose, they can be handled as a group in exactly the same manner as individual alarms, for example, respiration rate too high.

Moreover, the process 30 may comprise, for example, in a fourth step, an input 34 of a second user action or of an action for suppressing the alarm. The apparatus can be brought by means of a second user action into a state in which it does not generate an acoustic alarm over a defined time, for example, with an audio off function or silence function.

The process 30 may comprise, for example, in a fifth step, a checking 35 of whether a frequency of a second user action has exceeded a predefined limit for an alarm or a predefined threshold value, without a first user action having been performed during the time period being considered. It can be checked whether an audio off/silence function or a second user action was performed for the existing alarm, for example, within the past 30 minutes, more frequently than 3 times, without an action having been performed at the apparatus or at the patient or without a first user action having been performed during this time period.

Further, the process 30 may comprise, for example, in a sixth step, a display 36 of a dialog for setting alarm limits and/or therapy adjusters. If the frequency of the second user action has exceeded the predefined limit, a dialog for adapting the alarm limits and/or therapy adjustments can be opened with the actuation of the acoustic alarm suppression. The dialog may be displayed, for example, on a patient monitor, which may be connected to the device 10.

Further details and aspects are mentioned in connection with the exemplary embodiments described above or below. The exemplary embodiment shown in FIG. 3 may comprise one or more additional optional features.

Functions of different elements shown in the figures as well as the designated function blocks may be implemented in the form of dedicated hardware, e.g., of "a signal provider," of "a signal processing unit," of "a processor," of "a control," etc., as well as as hardware capable of executing software in connection with corresponding software. In case of provision by a processor, the functions may be provided by an individual dedicated processor, by an individual processor used in a shared manner or by a plurality of individual processors, some of which or all of which may be used in a shared manner. However, the term "processor" or "control" is far from being limited to hardware capable exclusively of executing software, but it may comprise digital signal processor hardware (DSP hardware; DSP=Digital Signal Processor), network processor, application-specific integrated circuit (ASIC=Application Specific Integrated Circuit), field-programmable logic array (FPGA=Field Programmable Gate Array), read-only memory (ROM=Read Only Memory) for storing software, direct access memory (RAM=Random Access Memory) and nonvolatile memory device (storage). Other hardware, conventional and/or user-specific, may be included as well.

A block diagram may represent, for example, a coarse circuit diagram, which implements the basic principles of the disclosure. A flow chart, a flow diagram, a state transition diagram, a pseudocode and the like may similarly represent different processes, operations or steps, which are represented, for example, essentially in computer-readable medium and are thus executed by a computer or processor, regardless of whether such a computer or processor is explicitly shown. Processes disclosed in the description or in the patent claims may be implemented by a component, which has a device for executing each of the respective steps of these processes.

It is apparent that the disclosure of a plurality of steps, processes, operations or functions disclosed in the description or in the claims shall not be considered to be in the defined order, unless this is explicitly or implicitly stated otherwise, e.g., for technical reasons. Therefore, these are not limited to a defined order by the disclosure of a plurality of steps or functions, unless these steps or functions are not replaceable for technical reasons. Further, an individual step, function, process or operation may include in some examples a plurality of partial steps, partial functions, partial processes or partial operations and./or may be divided into same. Such partial steps may be included and be part of the disclosure of this individual step unless they are explicitly excluded.

While specific embodiments of the invention have been shown and described in detail to illustrate the application of the principles of the invention, it will be understood that the invention may be embodied otherwise without departing from such principles.

LIST OF REFERENCE NUMBERS

10 Device;
11 Processing device;
12 Interface;
20 Process;
21 Generation of at least one adapted alarm condition of an alarm concerning at least one parameter triggering the alarm;
22 Determination of whether an alarm frequency exceeds a limit value;
30 Process;
31 Input of an alarm, of at least one corresponding measured value, and/or of at least one corresponding alarm limit;
32 Input of a first user action;
33 Analysis of a frequency of user actions;
34 Input of a second user action;
35 Checking whether a frequency of a second user action has exceeded a predefined limit for an alarm without a first user action having been performed during the time period being considered;
36 Display of a dialog for setting alarm limits and/or therapy adjusting devices.

What is claimed is:

1. A device for providing a suggestion for at least one adapted alarm condition for a user in a medical system, the device comprising:
a processing device configured to generate at least one adapted alarm condition of an alarm concerning at least one parameter triggering the alarm, the generated adapted alarm condition being provided for adapting the at least one alarm condition when an alarm frequency exceeds a limit value; and
an interface operatively connected to the processing device and configured to provide the generated adapted alarm condition as a suggestion for adapting the at least one alarm condition, the processing device being further configured to generate the at least one adapted alarm condition when a frequency of actions taken for suppressing the alarm exceeds a predefined threshold value.

2. A device in accordance with claim 1, wherein:
the processing device is further configured to indicate at least one possible cause of the alarm and at least one possibility for eliminating the at least one possible cause of the alarm when the alarm frequency exceeds the limit value; and
the interface is further configured to provide the at least one possible cause ofthe alarm and the at least one possibility for eliminating the at least one possible cause of the alarm.

3. A device in accordance with claim 2, wherein the processing device is further configured to generate the at least one adapted alarm condition when no user action takes place for eliminating the at least one possible cause of the alarm within a predefined time period.

4. A device in accordance with claim 3, wherein the processing device is further configured to determine, on the basis of video data, whether at least one user action has taken place for eliminating the at least one possible cause of the alarm.

5. A device in accordance with claim 3, wherein the processing device is further configured to store information on whether a user action has taken place for eliminating the at least one possible cause of the alarm.

6. A device in accordance with claim 1, wherein the processing device is further configured to store at least one alarm, a time of the at least one alarm, at least one alarm condition of the at least one alarm, vital data of a patient and/or the actions taken to suppress the at least one alarm.

7. A device in accordance with claim 6, wherein the processing device is further configured to determine a trend of a vital parameter based on vital data of the patient.

8. A device in accordance with claim 1, wherein the processing device is further configured to classify alarms in a classification based on at least one parameter triggering the alarm.

9. A device in accordance with claim 8, wherein the processing device is further configured to store the classification and to check whether a plurality of actions taken to suppress the alarm have taken place in case of an identical classification.

10. A device in accordance with claim 1, wherein the interface is further configured to receive an alarm signal and the processing device is further configured to determine information concerning the alarm frequency based on the alarm signal.

11. A process for providing a suggestion for adapted alarm conditions for a user of a medical system, the process comprising:
generating, with processing device, at least one adapted alarm condition of an alarm concerning at least one parameter triggering the alarm, which adapted alarm condition is to offer to the user a possibility of adapting the at least one alarm condition when an alarm frequency exceeds a limit value; and
providing the generated adapted alarm condition as a suggestion for adapting the alarm condition of the alarm to the user via an interface operatively connected to the processing device, the processing device being further configured to generate the at least one adapted alarm condition when a frequency of actions taken for suppressing the alarm exceeds a predefined threshold value.

12. A process in accordance with claim 11, wherein:
the processing device is further configured to indicate at least one possible cause of the alarm and at least one possibility for eliminating the at least one possible cause of the alarm when the alarm frequency exceeds the limit value; and
the interface is further configured to provide the at least one possible cause of the alarm and the at least one possibility for eliminating the at least one possible cause of the alarm.

13. A process in accordance with claim 12, wherein the processing device is further configured to generate the at least one adapted alarm condition when no user action takes place for eliminating the at least one possible cause of the alarm within a predefined time period.

14. A process in accordance with claim 13, wherein the processing device is further configured to determine, on the basis of video data, whether at least one user action has taken place for eliminating the at least one possible cause of the alarm.

15. A process in accordance with claim 13, wherein the processing device is further configured to store information on whether a user action has taken place for eliminating the at least one possible cause of the alarm.

16. A process in accordance with claim 11, wherein the processing device is further configured to store at least one alarm, a time of the at least one alarm, at least one alarm condition of the at least one alarm, vital data of a patient and/or the actions taken to suppress the at least one alarm.

17. A process for providing a suggestion for at least one adapted alarm condition for a user in a medical system, the process comprising:
providing a device comprising a processing device configured to generate an adapted alarm condition of an alarm related to at least one parameter triggering the alarm when an alarm frequency exceeds a limit value and an interface operatively connected to the processing device and configured to provide the generated adapted alarm condition as a suggestion for adapting the at least one alarm condition, the processing device being further configured to generate the at least one adapted alarm condition when a frequency of actions taken for suppressing the alarm exceeds a predefined threshold value;
generating, with processing device, the adapted alarm condition when the alarm frequency exceeds the limit value; and
outputting the generated adapted alarm condition as a suggestion for adapting the alarm condition of the alarm to the user via the interface operatively connected to the processing device.

18. A process according to claim 17, further comprising providing a non-transitory computer readable media comprising a computer program with a program code for carrying out one or more of the process steps when the program code is executed on a computer comprising the processing device, on a processor of the processing device or on a programmable hardware component that comprises or forms a part of the processing device.

19. A device for providing a suggestion for at least one adapted alarm condition for a user in a medical system, the device comprising:
a processing device configured to generate at least one adapted alarm condition of an alarm concerning at least one parameter triggering the alarm, the generated adapted alarm condition being provided for adapting the at least one alarm condition when an alarm frequency exceeds a limit value; and
an interface operatively connected to the processing device and configured to provide the generated adapted alarm condition as a suggestion for adapting the at least one alarm condition, the processing device being further configured to classify alarms in a classification based on at least one parameter triggering the alarm, the processing device being further configured to store the classification and to check whether a plurality of actions taken to suppress the alarm have taken place in case of an identical classification.

* * * * *